United States Patent
García Salgado López et al.

(10) Patent No.: US 8,895,538 B2
(45) Date of Patent: Nov. 25, 2014

(54) COMBINATION AND COMPOSITION THAT CONTAINS AN ANTIMICROBIAL, A GLUCOCORTICOID AND AN ANTIMYCOTIC

(75) Inventors: Raúl García Salgado López, Mexico City (MX); Gustavo Barranco Hernández, Mexico City (MX)

(73) Assignee: Laboratories Senosiain S.A. de C.V., Mexico City (MX)

( * ) Notice: Subject to any disclaimer, the term of this patent is extended or adjusted under 35 U.S.C. 154(b) by 139 days.

(21) Appl. No.: 13/496,164

(22) PCT Filed: Sep. 14, 2010

(86) PCT No.: PCT/IB2010/002301
§ 371 (c)(1),
(2), (4) Date: Mar. 14, 2012

(87) PCT Pub. No.: WO2011/033361
PCT Pub. Date: Mar. 24, 2011

(65) Prior Publication Data
US 2012/0178727 A1    Jul. 12, 2012

(30) Foreign Application Priority Data
Sep. 15, 2009 (MX) .................. MX/a/2009/009884

(51) Int. Cl.
| | | |
|---|---|---|
| *A61K 31/575* | (2006.01) | |
| *A61K 45/06* | (2006.01) | |
| *A61K 31/4164* | (2006.01) | |
| *A61K 9/00* | (2006.01) | |
| *A61K 31/573* | (2006.01) | |
| *A61K 47/06* | (2006.01) | |
| *A61K 47/10* | (2006.01) | |
| *A61K 47/32* | (2006.01) | |

(52) U.S. Cl.
CPC ............. *A61K 45/06* (2013.01); *A61K 31/4164* (2013.01); *A61K 9/0014* (2013.01); *A61K 31/573* (2013.01); *A61K 47/06* (2013.01); *A61K 47/10* (2013.01); *A61K 47/32* (2013.01)
USPC ....................................... 514/170

(58) Field of Classification Search
CPC   A61K 31/575; A61K 31/4164; A61K 31/573
USPC ......................................... 514/170
See application file for complete search history.

(56) References Cited

FOREIGN PATENT DOCUMENTS

| EP | 0049468 A1 | 4/1982 |
|---|---|---|
| MX | 177199 | 3/1995 |
| MX | 262379 | 11/2008 |
| WO | WO 2010/106465 A1 | 9/2010 |
| WO | WO 2010/122475 A1 | 10/2010 |
| WO | WO 2010/122491 A1 | 10/2010 |

OTHER PUBLICATIONS

Anthony C. Chu Antibacterial/steroid combination therapy in infected eczema Acta Derm Venereol 2008; Suppl. 216: 28-34.*
"Diccionario de Especialidades Farmaceuticas," Mexico Edicion 2004, Retrieved from Internet URL: http://www.libreriamedica8a.com/productos/985.htm.
Anonimo, "Fucicort-Creme," Oct. 14, 2004, Retrieved from Internet URL: http://www.pharmazie.com/graphic/A/64/1-25564.pdf.
Franchi, "Treatment of dermatological conditions with a combination of an antibacterial agent, and antifungal agent and an antiinflammatory steroid," International Journal of Clinical Pharmacology, Therapy and Toxicology, 1985, vol. 23, No. 9, pp. 488-490.
Larsen at al., "An Efficient New Formulation of Fusidic Acid and Betamethasone 17-Valerate (Fucicort Lipid Cream) for Treatment of Clinicaly Infected Atopic Dermatitis," Acta Derm Venereol, 2007, vol. 87, No. 1, pp. 62-68.

* cited by examiner

*Primary Examiner* — Jennifer M Kim
(74) *Attorney, Agent, or Firm* — Birch, Stewart, Kolasch & Birch, LLP

(57) ABSTRACT

The present invention relates to a topical pharmaceutical composition that comprises the combination of an antimicrobial, a glucocorticoid, an antimycotic and pharmaceutically acceptable vehicles or excipients; the method for producing the composition and the use of said composition for treating localized dermatosis ailments.

10 Claims, No Drawings

COMBINATION AND COMPOSITION THAT CONTAINS AN ANTIMICROBIAL, A GLUCOCORTICOID AND AN ANTIMYCOTIC

TECHNICAL FIELD OF THE INVENTION

The instant invention has its application in the pharmaceutical field, particularly in the pharmaceutical combination and formulation field, and more particularly it refers to a topical pharmaceutical combination and composition comprising an antimicrobial, a glucocorticoid, an antimycotic and pharmaceutically acceptable vehicles or excipients; the instant invention is also related with the method for producing such combinations and formulations and the use of said composition in the treatment of localized dermatosis ailments.

BACKGROUND OF THE INVENTION

One of the main objectives when developing of pharmaceutical combinations and formulations for drug therapeutic administration consists in obtaining effective and efficient local effects, and with lower adverse effects. In this context, the present invention intends to provide a solution for attending localized dermatosis ailments accompanied with inflammation, concomitantly with infections caused by bacterial and mycotic organisms.

There are some patent documents in the state of the art, related with formulations for treating mycotic or bacterial infections involving inflammation. However, as will be further demonstrated, such documents do not solve the technical problem that is posed and solved in the instant application.

For example, Mexican Patent MX177199 discloses an antimycotic pharmaceutical composition for topical application, which can be a cream, ointment, lotion, solution or aerosol spray. Said composition comprises from 0.001 to 0.33% of betametasone dipropionate and from 0.01 to 10% by weight of clotrimazole. The composition is particularly used when the patient suffers from mycotic infection accompanied with inflammation.

The formulation disclosed in said document includes two active agents and at least eight excipients such as: dispersing agents, emulsifier y and moisturizers selected from mineral oil, petrolatum, cetoestearilic alcohol, propylene glycol and polietylene glycol; as well as buffer regulators such as hydrated monobasic sodium phosphate and phosphoric acid, and finally a preservative agent such as benzyl alcohol.

The mentioned document is not directed to solve the problem of attending localized dermatosis ailments accompanied with inflammation, concomitantly with infections caused by bacterial and mycotic organisms, because it only focuses on mycotic infections accompanied with inflammation. In other words, said document does not describe or suggest how to integrate an antimicrobial, a glucocorticoid and an antimycotic in a combination or in a formulation for treating localized dermatosis ailments, achieving a broader therapeutic spectrum without increasing the possibilities of secondary effects. Moreover, the inclusion of a plurality of 8 or more excipients, as in the case of patent MX177199, involves long processing times, high operational costs, and the use of an excessive amount of materials. The latter factor becomes evident with the fact that, as will be further demonstrated, the instant invention uses only five excipients. This represents almost a 50% saving in materials, which also involves reducing processing times and operational costs.

Corticosteroids in general, are classified by their potency as low, medium or high, depending on their therapeutic activity. Thus, the betametasone valerate salt has medium activity and the propionate salt is considered of high activity. Therefore, the combination of betametasone propionate and clotrimazole increases the probabilities of undergoing adverse reactions such as acneiform eruptions, allergic dermatitis, dryness, pruritus, purpura, among others. For the present invention, the use of a corticosteroid combined with clotrimazole and fusidic acid represents an advantage; the disclosed formulation and combination increase their therapeutic spectra without increasing the possibility of adverse effects.

The patent document MX262379 refers to a pharmaceutical composition which is solid at room temperature, comprising a dose unit with a therapeutically effective amount of a therapeutic agent. Said solid pharmaceutical composition exhibits a softening point between 30 and 35° C. when entering in continuous contact with the patient's skin area. The composition may include more than one active agent, among which fusidic acid or betametasone or clotrimazole can be considered, as therapeutic agents. It is worth mentioning that the said document does not disclose a single formulation which includes the three active agents at the same time. The combination of fusidic acid, betametasone and clotrimazole cannot be achieved by simple addition when mixing the components of the formulation or combination, as will be further demonstrated in the present invention. In addition, patent No. MX262379 refers to "a dose unit" and specifically to tablets, which is the essence of the invention claimed therein. As will be further disclosed below, both the combination and composition claimed in the instant application are directed, among others, to the topical application, whose advantages related with the formulation process, broad therapeutic spectrum and use of relatively few excipients, confer novelty and inventive step.

In the commerce, there are formulations comprising combinations of one or two of the active agents that constitute the cream of the instant invention. Such is the case of the combination of fusidic acid with betametasone or the combination of clotrimazole with betametasone, as well as the compositions of two of them in combination with a third agent, such as the composition of fusidic acid, betametasone and gentamicine or betametasone, clotrimazole and gentamicine.

In contrast with these compositions, the instant invention selects three active agents having a broad therapeutic range in the treatment of mycotic infections, inflammation and/or microbial infections. This combination or composition does not increase the adverse effects of the active agents, as may occur with the use of gentamicine, a broad-spectrum antimicrobial agent and which consequently is contraindicated in immunocompromised patients, or patients that are susceptible of undergoing severe mycotic infections, because its use increases the risk of growth of microorganisms that are not susceptible to gentamicine, including fungi.

All the aforementioned evidences the need of developing a topical combination and formulation for attending conditions such as dermatosis that involve inflammation concomitantly with infections caused by bacterial and mycotic organisms, which is physicochemically stable, of broad spectrum and which uses a reduced amount of excipients in order to save materials. The instant invention focuses mainly in solving such prior art deficiencies by means of the topical pharmaceutical combination and composition that will be described herein below.

SUMMARY OF THE INVENTION

In general, the instant invention provides a combination comprising an antimicrobial, a glucocorticoid, an antimycotic and pharmaceutically acceptable vehicles or excipients.

In a preferred embodiment, the instant invention provides a topical pharmaceutical combination and composition comprising an antimicrobial, a glucocorticoid, an antimycotic and pharmaceutically acceptable vehicles or excipients; the instant invention is also related with the method for producing such combinations and formulations, and the use of said composition in the treatment of localized dermatosis ailments.

The instant formulation surprisingly demonstrated that the combination or formulation for topical local administration, combining an antimicrobial agent, a glucocorticoid and an antimycotic, is therapeutically effective in the treatment of local conditions of inflammation, allergy, bacterial and mycotic infections, with a possible reduction of adverse effects.

Topical applications are well tolerated due to the administration convenience and transporting simplicity. For these reasons, the present combination or composition can be formulated in the form of cream, gel, ointment, paste or other pharmaceutical form of topical administration, among which cream is preferred.

In the instant invention, the preferred antimicrobial agent, is selected from fusidic acid in a preferred amount of from 5 mg to 80 mg per each 1000 mg of combination or composition.

The glucocorticoid may be selected from betametasone, preferably betametasone valerate, betametasone propionate and mixtures thereof, in an amount of from 0.1 mg to 20 mg per each 1000 mg of combination or composition.

The antimycotic is selected from a compound from the azole group, such as clotrimazole, imidazole, ketoconazole, miconazole, tionazole or another one with similar properties, and mixtures thereof. This active agent may be included in an amount of from 2.5 to 50 mg per each 1000 mg of combination or composition.

The use of the mentioned active agents must not be considered as limitative for the instant invention, because a person with ordinary skill in the art may use other active agents with similar activity, without departing from the spirit of the instant invention.

The excipients for carrying out the present invention are selected from a dispersing agent of the kind of propylene glycol, polyethylene glycol or glycol derivatives, liquid paraffin, vinyl acid polymers (Carbopol 980 or Carbopol 940), among others; moisturizing agent: glycerol, sorbitol, polyethylene glycol, among others; emulsifying agent: castor oil, Cremophor RH40, Novemer, acryloyldimethyl taurate polymer Optasense RMA 50, soy lecithin, polysorbates, among others; buffer regulator or modulator: organic excipients such as lactic acid, triethanolamine and others; and/or a vehicle such as purified water.

Within the range of the mentioned excipients, several excipients with equivalent functions to the required ones and/or mixtures thereof, were assayed.

In a preferred embodiment, the instant invention provides a process for preparing a topical composition for the treatment of localized dermatosis ailments which comprises the following steps:
  1. In a container, add water and adjust pH mainly to an acid nature, between 4.0 and 5.0, and disperse a dispersing agent in this solution (Mixture A).
  2. In another container, add dispersing agent, moisturizing agent and the emulsifying agent.
  3. Once an homogeneous mixture of these components is obtained, disperse therein each one of the active agents in the following order: antimicrobial agent, antimycotic agent and lastly, the glucocorticoid (Mixture B).
  4. Once Mixture B is homogeneous, add Mixture A to Mixture B under vigorous stirring.
  5. Stir until obtaining a homogeneous mixture.

The ranges and amounts of the active agents and excipients used for the formulation, and consequently for the process for its manufacture, are specified below in the detailed description of the invention.

DETAILED DESCRIPTION OF THE INVENTION

A topical combination or formulation of fusidic acid, betametasone and clotrimazole allows attending the dermatosis and inflammation ailments; these conditions can be complicated with infections caused by bacterial and/or mycotic microorganisms. The undergoing skin ailments are, among others: psoriasis, contact dermatitis, eczema, neurodermatitis, intertrigo, anogenital dermatitis, senile pruritus or another one originated by bacteria, yeasts or fungi.

Drug absorption through skin is regulated by the skin characteristics and by the drug liposolubility. The instant invention is intended for direct application in skin, trying to obtain a localized and rapid onset on the occurring inflammation and infection. Depending on the body zone, skin pH is between 4.2 and 5.9 in the surface, the middle value being pH=5.5. The instant invention has an acid pH between 4 and 7, and is well tolerated by healthy and damaged skin.

Fusidic acid is a substance obtained from the *Fusidium coccineum* fermentation. It has a pH interval between 4.7 and 4.9, it is very sensitive to temperature variations, must be kept between 2 and 8° C., has a melting point between 192° and 193° C. It is soluble in alcohol, acetone, chloroform, pyridine, dioxane; it is almost insoluble in water, slightly soluble en ether and hexane. It is used in topical formulations for treating local topical infections.

When administered in combination with another active agent, it may exhibit stability problems, basically if the other components are not resistant to pH variations. Laboratory assays have demonstrated that its stability is greatly reduced in the presence of acid substances. This renders difficulties in formulating a pharmaceutical composition wherein fusidic acid coexists with other active agents without affecting the stability of each component.

Betametasone is a glucocorticoid that is almost insoluble in water. The betametasone valerate salt has a melting point between 183 and 184° C. It must be protected from light during its storage, and must be preserved at a temperature between 2 and 30° C. The betametasone valeate action is produced within the cell, where it binds to specific receptors, migrating subsequently to the nucleus. In the DNA it produces an anti-inflammatory, antiproliferative and immunosuppressive response. Being a steroid, it produces vasoconstriction, thereby prolonging the permanence of the antimycotic agent in the application site.

Clotrimazole is a weak base, an imidazole derivative, almost insoluble in water, melting point 147° to 149°. It is rapidly hydrolised in acid solution at high temperature. It must be protected from light during storage. It exhibits an LD50 in mice and rats of 923 and 708 mg/Kg, respectively, when administered orally. In topical applications it may be absorbed from 3 to 10% of the dose.

In a preferred embodiment, the instant invention may be a cream, paste, ointment, gel or other, which includes at least three active agents. From these formulations, the preferred one is a cream: a well-tolerated and easily washable formulation. Its localized topical action in the application area reduces even more the possibility of adverse effects originated by the administration of drugs of systemic application.

It is not easy to obtain a formulation including the three agents fusidic acid, betamethasone and clotrimazole, because it is not achieved by simple mixture of these ingredients. A technical problem involving a formulation with active agents having different physicochemical properties and which provoke formulation instability, must be solved. From this technical problem it is concluded that the order of addition of the active agents and the selected excipients have a great importance in obtaining formulation stability. In this invention, the excipients form a multi-compartment system that allows for the coexistence of the active ingredients.

The formulation and administration of pharmaceutical combinations is not easy, because when two or more active agents are administered in a single pharmaceutical form, it may result in degradation or active agent interactions, adverse reactions, secondary effects, as well as technological problems resulting from the physicochemical interaction of the active agents and excipients.

The pharmaceutical composition of fusidic acid, betamethasone valerate and clotrimazole, is stable at an acid pH between 4 and 7, a pH that is well tolerated by the skin (which has an average pH of 5.5).

The instant formulation surprisingly demonstrated that the composition of local topical administration with the combination of fusidic acid, betamethasone valerate and clotrimazole, is therapeutically effective in the treatment of local conditions of inflammation, allergy, bacterial and mycotic infections, with a possible reduction of the adverse effects, in comparison with formulations of systemic administration or formulations that exhibit a broad antibacterial spectrum.

The use of betamethasone valerate, which is a steroid, produces vasoconstriction, which prolongs the antimycotic permanence in the application site. This effect is necessary due to the micellia-spore cycle in mycotic infections. With this formulation, it is possible to take advantage of the synergic effect of the glucocorticoid and the antimycotic.

The topical presentation of the instant invention is well tolerated, it does not irritate skin, it is stable to environmental factors, it has an appropriate consistency for being extended over the skin, with acceptable organoleptic properties. It does not produce dehydration, nor allows for losing natural fat, which is necessary for the skin.

These formulations are more easily administered in persons that do not wish to receive or cannot get a parenterally or orally administered treatment, and which suffer from localized injuries and undergo inflammation and/or bacterial and/or mycotic infections. According to the aforementioned, it is appreciated that the utility spectrum, as well as the antibacterial, antimycotic, anti-inflammatory and antiallergic spectra, may allow reducing a treatment, depending on the extension, location and clinical response of the patient.

The effectiveness of the combination of the active agents, as well as the certainty of having a pharmaceutical form with all the quality criteria, are very important factors for allowing patients to benefit from an appropriate treatment for these conditions.

The challenge when developing the present invention consisted in obtaining of a stable, safe and therapeutically effective topical pharmaceutical composition, which includes drugs that are physicochemically different therebetween, as is the case of fusidic acid, betamethasone valerate and clotrimazole.

Fusidic acid, due to its physicochemically properties, is very sensitive to pH variations. Clotrimazole is more stable at slightly basic pH, between 7 and 8. Betamethasone valerate is more stable at slightly acid pH, between 5 and 7 and is the most sensitive one to environmental conditions, i.e., even when the three ingredients must be protected from light and temperature, betamethasone may suffer degradation more easily during storage and even during the formulation manufacturing process.

Laboratory assays were carried out for verifying the sensitivity, solubility and stability of the active agents at different pH conditions. Thus, their stability was tested at different pH conditions. Due to the sensitivity of the active agents, the addition order of these components, as well as the excipient and vehicle selection are of great importance for avoiding degradation or incompatibilities of said active agents.

Examples of representative topical formulations of the present invention, are shown hereinbelow.

EXAMPLE 1

Cream Topical Formulation

Table 1 shows the topical general formulation in the form of a cream having the combination of fusidic acid, betamethasone valerate and clotrimazole. Table 2 illustrates examples of formulations comprising fusidic acid, betamethasone valerate and clotrimazole, wherein the weight amount of the active agents, vehicles and/or excipients, can be employed between the mentioned use ranges without limiting their use.

TABLE 1

TOPICAL GENERAL CREAM FORMULATION

| Ingredient | Percent use ranges/ per each 100.0 mg of composition | Use ranges in mg/per 1 g of composition |
| --- | --- | --- |
| Fusidic acid | 0.5-8.0 | 5-80 |
| Clotrimazole | 0.25-5.0 | 2.5-50 |
| Betametasone Valerate | 0.01-2.0 | 0.1-20 |
| Dispersing agent 1 | 5.0-6.5 | 50-65 |
| Emulsifying agent | 3.2-4.5 | 32-45 |
| Dispersing agent 2 | 0.3-0.5 | 3-5 |
| Moisturizing agent | 2.5-3.5 | 25-35 |
| Buffer regulator | — | — |
| Purified water q.s. | 74.0-84.0 | 740-840 |
| Total | 100.0 | 1000 |

TABLE 2

TOPICAL GENERAL CREAM FORMULATION

| | Percent use ranges/per 1 g of composition | | |
| --- | --- | --- | --- |
| Ingredient | Formulation 1 | Formulation 2 | Formulation 3 |
| Fusidic acid | 5 | 20 | 80 |
| Clotrimazole | 2.5 | 10 | 50 |
| Betametasone valerate | 0.1 | 0.61 | 20 |
| Liquid paraffin | 65 | 60 | 50 |
| Optasense RMA 50 | 45 | 40 | 32 |
| Carbopol 940 | 5 | 4 | 3 |
| Glycerol | 35 | 32 | 25 |
| Lactic acid | — | — | — |
| Purified water q.s. | 840 | 833 | 740 |
| Total | 1000 | 1000 | 1000 |

The method for preparing the composition will be further described below. The following example, without being limitative, illustrates the objective of the invention by means of a topical formulation.

1. Weight the components of the formulation
2. In a container of appropriate volume, add 300 g water, adjust pH between 4.0 and 5.0 with 0.01% lactic acid solution, disperse Carbopol 980 in this solution (Mixture A).
3. In another container, place the weighted amount of dispersing agent 1 which can be liquid paraffin, the moisturizing agent which can be glycerol, and add the emulsifying agent which can be Optasense RMA 50 polymer.
4. Once a homogeneous mixture of these components is obtained, disperse therein the weighted amount of the active agents in the following order: fusidic acid, clotrimazole and lastly, the corticoid (Mixture B).
5. Once Mixture B is homogeneous, add Mixture A to Mixture B under vigorous stirring between 5000 and 7000 r.p.m.
6. Stir until a homogeneous mixture is obtained.
7. Determine the pH value of the cream to a 10% sample.

The present topical formulation was subjected to a stability test in which the formulation was exposed to several temperature and humidity conditions, with the intention to prove the stability of the pharmaceutical composition.

Periodical tests of the aspect, concentration and pH were performed during the study and upon finalization. The results of the stability assay performed to the topical composition, are shown herein below.

Three different batches were prepared, based on formulation 2 (shown above in Table 2).

The formulations were identified as A, B and C, respectively.

TABLE 3

FORMULATION TESTING

| Determination | Specification |
|---|---|
| Appearance | White-colored cream, homogeneous appearance, free of strange particles, with low viscosity |
| Evaluation | 90% and 110% |
| pH | Between 4.0 and 7.0 (determined to a 10.0% sample in water) |

TABLE 4

STABILITY RESULTS OF FORMULATIONS A, B AND C.

| | | | Valoración | | | |
|---|---|---|---|---|---|---|
| | Stability Conditions | Appearance | FA | C | BV | pH |
| Formulation A | | | | | | |
| Initial | Room Temperature | Complies specifications | 104.0 | 106.6 | 104.7 | 6.2 |
| 20 days | 30° C. Temp. | Complies specifications | 98.0 | 103.1 | 101.6 | 6.8 |
| | 40 or 50° C. Temp. | Complies specifications | 99.5 | 105.8 | 94.7 | 6.6 |
| 60 days | 30° C. Temp. | Complies specifications | 94.1 | 98.7 | 99.2 | 6.9 |
| | 40 or 50° C. Temp. | Complies specificactions | 91.2 | 94.3 | 90.7 | 6.7 |
| Formulation B | | | | | | |
| Initial | Room Temperature | Complies specifications | 93.8 | 98.9 | 99.3 | 4.9 |
| 20 days | Temp. 30° C. | Complies specifications | 97.8 | 101.4 | 101.6 | 5.2 |
| | Temp. 40 or 50° C. | Complies specifications | 97.2 | 94.5 | 94.9 | 5.4 |
| 60 days | Temp. 30° C. | Complies specifications | 92.9 | 97.5 | 99.0 | 5.2 |
| | Temp. 40 or 50° C. | Complies specifications | 90.2 | 91.9 | 90.0 | 5.5 |
| Formulation C | | | | | | |
| Initial | Room Temperature | Complies specifications | 94.6 | 94.9 | 95.0 | 5.2 |
| 20 days | Temp. 30° C. | Complies specifications | 94.0 | 93.3 | 92.1 | 5.2 |
| | Temp. 40 or 50° C. | Complies specifications | 96.8 | 90.9 | 75.3 | 5.3 |
| 60 days | Temp. 30° C. | Complies specifications | 91.6 | 91.3 | 92.3 | 5.3 |
| | Temp. 40 or 50° C. | Complies specifications | 90. | 90.5 | 90.1 | 5.4 |

FA = Fusidic acid, C = Clotrimazole and BV = Betametasone valerate

From the stability study results of it can be appreciated that the cream formulation is very sensitive to temperature and pH variations, during its preparation and storage. These variations may provoke degradation of the active agents or problems during the cream manufacture.

Betametasone valerate is the most sensitive active agent when being exposed to changes in the manufacture and storage conditions, because during storage, the betametasone 17-valerate salt contains impurities of betametasone 21-valerate. For this reason, the formulation is prepared at low temperature conditions and with pH stabilizers. In addition, betametasone is the last active agent to be added to the formulation, to avoid exposing it to the stress produced during the manufacture process.

When the above-mentioned operational parameters are controlled, problems are often encountered, such as active agent degradation, mainly of betametasone, or loss of the cream integrity and phase separation.

The study results demonstrated that a composition having an unexpected high stability was obtained, since the physicochemical tests were satisfactory.

The analysis of the performed tests, such as formulation appearance, demonstrate that the cream remains intact while performing the evaluation and at the end of the test, without impurity presence, phase separation or color migration; with regard to the active agent content, these ingredients remained within the allowed specifications to accomplish therapeutic activity.

The manufacturing process of the present invention, at low temperature conditions, guarantees content uniformity of the composition, appropriate release of the active agents, formulation stability and acceptability of the combination.

For the above-mentioned reasons, the instant invention presents a pharmaceutical composition comprising three active agents having different but complementary therapeutic activity, which do not compete for the action sites within the organism.

Considering the aforementioned, the instant invention discloses a physicochemically stable, safe and effective pharmaceutical composition, which achieves a multicompartimental acid-base equilibrium and which not interferes with the immediate release of the active agents, obtaining the therapeutic effect.

The use of the active agents is not limitative to the previously-indicated ones, since the formulation can include the pharmaceutically effective salts of the active agents of the formulation or other antimicrobials, anti-inflammatory agents, steroids o antimycotics.

The invention has been sufficiently described in such a way that a person with ordinary skills in the art can reproduce and obtain the results mentioned in this specification. However, any person with skills in the state of the art, related with the instant invention, can be capable of performing modifications that are not described in the instant application. However, if the application of these modifications in a particular composition requires the matter claimed in the following claims, these compositions must be comprised within the scope of the present invention.

The invention claimed is:

1. A pharmaceutical composition for topical application, useful in the treatment of localized dermatosis ailments accompanied with inflammation, concomitantly with infections caused by bacterial and mycotic organisms, comprising, per each 100 mg of composition: from 0.5 to 8.0 mg of fusidic acid; from 0.25 to 5.0 mg of clotrimazole; from 0.01 to 2.0 mg of betamethasone salt; from 5.0 to 6.5 mg of a first dispersing agent; from 3.2 to 4.5 mg of an emulsifying agent; from 0.3 to 0.5 mg of a second dispersing agent; from 2.5 to 3.5 mg of a moisturizing agent; and from 74.0 to 84.0 mg of water.

2. The pharmaceutical composition in accordance with claim 1, further wherein it is a composition for topical application selected from cream, gel, ointment, paste or another pharmaceutical form.

3. The pharmaceutical composition in accordance with claim 1, wherein the betamethasone salt is selected from betamethasone valerate and/or propionate.

4. The pharmaceutical composition in accordance with claim 1, wherein the composition is stable at a pH between 4 and 7.

5. A process for preparing the pharmaceutical composition for topical application useful in the treatment of localized dermatosis ailments accompanied with inflammation, concomitantly with infections caused by bacterial and mycotic organisms, in accordance with claim 1, comprising the following steps: (i) preparing Mixture A in a container by adding water and adjusting pH between 4.0 and 5.0 and dispersing the first dispersing agent in this solution; (ii) in another container placing the second dispersing agent, the moisturizing agent and adding the emulsifying agent; (iii) once the mixture of these components is homogeneous, dispersing therein each one of the following active agents in the following order: fusidic acid, clotrimazole and lastly the betamethasone salt, in order to obtain Mixture B; (iv) homogenizing Mixture B; (v) adding Mixture A to Mixture B under vigorous stirring; and (vi) stir until obtaining an homogeneous mixture.

6. A method of treating localized dermatosis ailments accompanied with inflammation, concomitantly with infections caused by bacterial and mycotic organisms, comprising: administering an effective amount of the pharmaceutical composition of claim 1 to a patient in need thereof.

7. The method of claim 6, wherein the pharmaceutical composition is adapted for topical application as a cream, gel, ointment, paste or other pharmaceutical form.

8. The method of claim 6, wherein the betamethasone salt is selected from betamethasone valerate and/or propionate.

9. The method of claim 6, wherein the ailments are: local conditions of inflammation, allergy, bacterial and mycotic infections, psoriasis, contact dermatitis, eczema, neurodermatitis, intertrigo, anogenital dermatitis, or senile pruritus.

10. The process in accordance with claim 5, wherein the betamethasone salt is at least one selected from the group consisting of betamethasone valerate and propionate.

* * * * *

UNITED STATES PATENT AND TRADEMARK OFFICE
CERTIFICATE OF CORRECTION

PATENT NO. : 8,895,538 B2
APPLICATION NO. : 13/496164
DATED : November 25, 2014
INVENTOR(S) : Raúl García-Salgado López et al.

It is certified that error appears in the above-identified patent and that said Letters Patent is hereby corrected as shown below:

ON THE TITLE PAGE:

At item (73), Assignee, change "Laboratories Senosiain S.A. de C.V., Mexico City (MX)" to --Laboratorios Senosiain S.A. de C.V., Mexico City (MX)--.

Signed and Sealed this
Twenty-first Day of April, 2015

Michelle K. Lee
*Director of the United States Patent and Trademark Office*